(12) United States Patent
Livshits et al.

(10) Patent No.: US 6,737,255 B2
(45) Date of Patent: May 18, 2004

(54) MUTANT ILVH GENE AND METHOD FOR PRODUCING L-VALINE

(75) Inventors: Vitaliy Arkadyevich Livshits, Moscow (RU); Vera Georgievna Doroshenko, Moscow (RU); Nataliya Vasilyevna Gorshkova, Moscow (RU); Alla Valentinovna Belaryeva, Moscow (RU); Lirina Valeryevna Ivanovskaya, Moscow (RU); Evgeni Moiseevich Khourges, Moscow (RU); Valery Zavenovich Akhverdian, Moscow (RU); Mikhail Markovich Gusyatiner, Moscow (RU); Yury Ivanovich Kozlov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 41 days.

(21) Appl. No.: 09/761,782

(22) Filed: Jan. 18, 2001

(65) Prior Publication Data

US 2002/0037562 A1 Mar. 28, 2002

(30) Foreign Application Priority Data

Jan. 26, 2000 (RU) .......................................... 00101678

(51) Int. Cl.[7] ................................................. C12P 13/08
(52) U.S. Cl. ..................... 435/115; 536/23.2; 536/23.7; 435/252.1; 435/252.3
(58) Field of Search ............................. 435/115, 252.1, 435/252.3, 252.31, 471, 441, 476, 477; 536/23.2, 23.7, 23.1

(56) References Cited

U.S. PATENT DOCUMENTS

| | | |
|---|---|---|
| 5,175,107 A | 12/1992 | Debabov et al. |
| 5,534,421 A | 7/1996 | Livshits et al. |
| 5,538,873 A | 7/1996 | Debabov et al. |
| 5,631,157 A | 5/1997 | Debabov et al. |
| 5,658,766 A | 8/1997 | Livshits et al. |
| 5,705,371 A | 1/1998 | Debabov et al. |
| 5,976,843 A | 11/1999 | Debabov et al. |
| 6,132,999 A | 10/2000 | Debabov et al. |
| 6,165,756 A | 12/2000 | Debabov et al. |

FOREIGN PATENT DOCUMENTS

| | | |
|---|---|---|
| EP | 0 356 739 A1 | 3/1990 |
| EP | 0 436 886 A1 | 7/1991 |
| WO | WO96/06926 | 3/1996 |

OTHER PUBLICATIONS

Smith et al. Complete Genome Sequence of Methanobacterium thermoautotrophicum DH: Functional Analysis and Comparative Genomics. J. Bacteriol. (1997) 179(22): 7135–7155.*
Grimaldi et al. A mutation affecting the valine sensitivity of the acetohydroxyacid synthase III isozyme in E. coli K–12. Biochem. Biophys. Res. Comm. (1981) 101(4): 1233–1240.*
Maria Vyazmenskiy, et al., Biochemistry, vol. 35, No. 32, pp. 10339–10346, "Isolation and Characterization of Subunits of Acetohydroxy Acid Synthase Isozyme III and Reconstitution of the Holoenzyme", 1996.
Maurilio De Felice, et al., Journal of Bacteriology, vol. 120, No. 3, pp. 1058–1067, "Regulation of the Pool Size of Valine in *Escherichia coli* K–12", Dec. 1974.
John Guardiola, et al., vol. 120, No. 1, pp. 536–538, "Mutant of *Escherichia coli* K–12 Missing Acetolactate Synthase Activity", Oct. 1974.
Maurilio De Felice, et al., vol. 120, No. 3, pp. 1068–1077, "Structural Genes for a Newly Recognized Acetolactate Synthase in *Escherichia coli* K–12", Dec. 1974.
C. Squires et al., "Molecular Structure of ILVIH and its Evolutionary Relationship to ILVG in *Escherichia coli* K–12", Nucleic Acids Research, vol. 11, No. 15, Aug. 11, 1983, pp. 5299–5313.
C. J Bult. et al., "Methanococcus Jannaschii Section 15 PF 150 of the Complete Genome". Database EMBL. Database accession No. U67473, Aug. 26, 1996.

* cited by examiner

Primary Examiner—Ponnathapu Achutamurthy
Assistant Examiner—Kathleen Kerr
(74) Attorney, Agent, or Firm—Oblon, Spivak, McClelland, Maier & Neustadt, PC

(57) ABSTRACT

The present invention provides an isolated DNA molecule encoding a small subunit of acetohydroxy acid synthase isozyme III originating from *Escherichia coli* and mutants of *Escherichia coli* acetohydroxy acid synthase isozyme III, which are free from inhibition by L-valine an can catalyze the conversion of: (a) pyruvate to α-acetolactate and (b) α-ketobutyrate and pyruvate to α-aceto-a-hydroxybutyrate. The present invention also provides methods for producing L-valine by fermentation of a bacterium harboring the novel DNA molecule and/or expressing the mutant acetohydroxy acid synthase isozyme III.

16 Claims, 1 Drawing Sheet

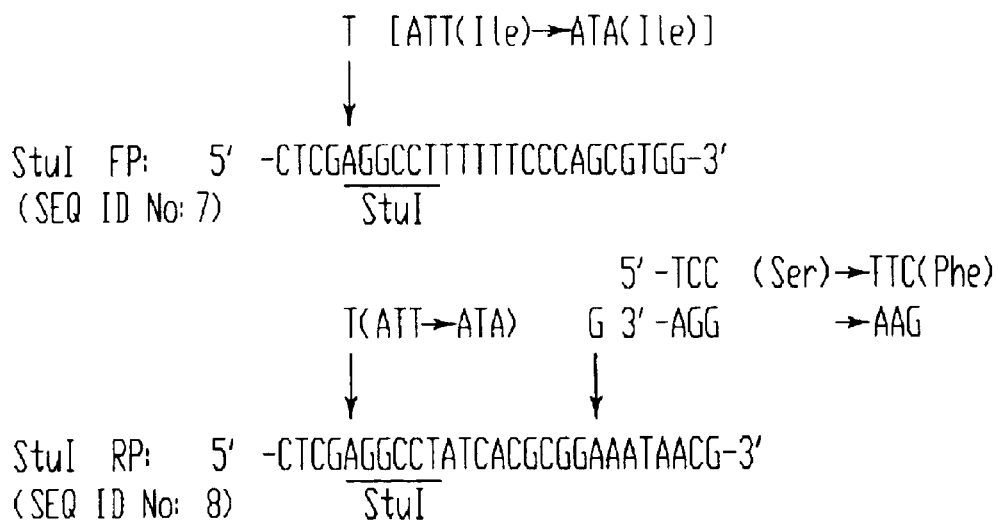

SEQUENCE LISTING

<160> NUMBER OF SEQ ID NOS: 8

<210> SEQ ID NO 1
<211> LENGTH: 492
<212> TYPE: DNA
<213> ORGANISM: Escherichia coli
<220> FEATURE:
<221> NAME/KEY: CDS
<222> LOCATION: (1)..(489)
<223> OTHER INFORMATION:

<400> SEQUENCE: 1

```
atg cgc cgg ata tta tca gtc tta ctc gaa aat gaa tca ggc gcg tta      48
Met Arg Arg Ile Leu Ser Val Leu Leu Glu Asn Glu Ser Gly Ala Leu
1               5                   10                  15 tcc cgc gtg att ggc ctt ttt tcc cag cgt ggc tac aac att gaa agc      96
Ser Arg Val Ile Gly Leu Phe Ser Gln Arg Gly Tyr Asn Ile Glu Ser
                20                  25                  30 ctg acc gtt gcg cca acc gac gat ccg aca tta tcg cgt atg acc atc     144
Leu Thr Val Ala Pro Thr Asp Asp Pro Thr Leu Ser Arg Met Thr Ile
            35                  40                  45 cag acc gtg ggc gat gaa aaa gta ctt gag cag atc gaa aag caa tta     192
Gln Thr Val Gly Asp Glu Lys Val Leu Glu Gln Ile Glu Lys Gln Leu
        50                  55                  60 cac aaa ctg gtc gat gtc ttg cgc gtg agt gag ttg ggg cag ggc gcg     240
His Lys Leu Val Asp Val Leu Arg Val Ser Glu Leu Gly Gln Gly Ala
65                  70                  75                  80 cat gtt gag cgg gaa atc atg ctg gtg aaa att cag gcc agc ggt tac     288
His Val Glu Arg Glu Ile Met Leu Val Lys Ile Gln Ala Ser Gly Tyr
                85                  90                  95 ggg cgt gac gaa gtg aaa cgt aat acg gaa ata ttc cgt ggg caa att     336
Gly Arg Asp Glu Val Lys Arg Asn Thr Glu Ile Phe Arg Gly Gln Ile
                100                 105                 110 atc gat gtc aca ccc tcg ctt tat acc gtt caa tta gca ggc acc agc     384
Ile Asp Val Thr Pro Ser Leu Tyr Thr Val Gln Leu Ala Gly Thr Ser
            115                 120                 125
```

```
ggt aag ctt agt gca ttt tta gca tcg att cgc gat gtg gcg aaa att    432
Gly Lys Leu Ser Ala Phe Leu Ala Ser Ile Arg Asp Val Ala Lys Ile
    130             135                 140 gtg gag gtt gct cgc tct ggt gtg gtc gga ctt tcg cgc ggc gat aaa    480
Val Glu Val Ala Arg Ser Gly Val Val Gly Leu Ser Arg Gly Asp Lys
145             150                 155                 160 ata atg cgt tga                                                    492
Ile Met Arg
```

<210> SEQ ID NO 2
<211> LENGTH: 163
<212> TYPE: PRT
<213> ORGANISM: Escherichia coli

<400> SEQUENCE: 2

```
Met Arg Arg Ile Leu Ser Val Leu Leu Glu Asn Glu Ser Gly Ala Leu
1               5                   10                  15

Ser Arg Val Ile Gly Leu Phe Ser Gln Arg Gly Tyr Asn Ile Glu Ser
            20                  25                  30

Leu Thr Val Ala Pro Thr Asp Asp Pro Thr Leu Ser Arg Met Thr Ile
        35                  40                  45

Gln Thr Val Gly Asp Glu Lys Val Leu Glu Gln Ile Glu Lys Gln Leu
    50                  55                  60

His Lys Leu Val Asp Val Leu Arg Val Ser Glu Leu Gly Gln Gly Ala
65                  70                  75                  80

His Val Glu Arg Glu Ile Met Leu Val Lys Ile Gln Ala Ser Gly Tyr
                85                  90                  95

Gly Arg Asp Glu Val Lys Arg Asn Thr Glu Ile Phe Arg Gly Gln Ile
            100                 105                 110

Ile Asp Val Thr Pro Ser Leu Tyr Thr Val Gln Leu Ala Gly Thr Ser
        115                 120                 125

Gly Lys Leu Ser Ala Phe Leu Ala Ser Ile Arg Asp Val Ala Lys Ile
    130                 135                 140

Val Glu Val Ala Arg Ser Gly Val Val Gly Leu Ser Arg Gly Asp Lys
145                 150                 155                 160

Ile Met Arg
```

<210> SEQ ID NO 3
<211> LENGTH: 18
<212> TYPE: DNA
<213> ORGANISM: Artificial Sequence
<220> FEATURE:
<223> OTHER INFORMATION: Synthetic DNA

<400> SEQUENCE: 3
gacatgaatg tctggttt                                                18

<210> SEQ ID NO 4
<211> LENGTH: 19
<212> TYPE: DNA
<213> ORGANISM: Artificial Sequence
<220> FEATURE:
<223> OTHER INFORMATION: Synthetic DNA

<400> SEQUENCE: 4
tcaacgcatt attttatcg                                               19

<210> SEQ ID NO 5
<211> LENGTH: 24
<212> TYPE: DNA

-continued

```
<213> ORGANISM: Artificial Sequence
<220> FEATURE:
<223> OTHER INFORMATION: Synthetic DNA

<400> SEQUENCE: 5
taaacgcgtt atcccgcgtg attg                                                24

<210> SEQ ID NO 6
<211> LENGTH: 24
<212> TYPE: DNA
<213> ORGANISM: Artificial Sequence
<220> FEATURE:
<223> OTHER INFORMATION: Synthetic DNA

<400> SEQUENCE: 6
gccacgcgtc tgattcattt tcga                                                24

<210> SEQ ID NO 7
<211> LENGTH: 25
<212> TYPE: DNA
<213> ORGANISM: Artificial Sequence
<220> FEATURE:
<223> OTHER INFORMATION: Synthetic DNA

<400> SEQUENCE: 7
ctcgaggcct tttttcccag cgtgg                                               25

<210> SEQ ID NO 8
<211> LENGTH: 27
<212> TYPE: DNA
<213> ORGANISM: Artificial Sequence
<220> FEATURE:
<223> OTHER INFORMATION: Synthetic DNA

<400> SEQUENCE: 8
ctcgaggcct atcacgcgga aataacg                                             27
```

MUTANT ILVH GENE AND METHOD FOR
PRODUCING L-VALINE

TECHNICAL FIELD

This invention relates to a method for producing L-valine by fermentation, particularly, a DNA coding for acetohydroxy acid synthase isozyme III which is free from feedback inhibition by L-valine, a microorganism which harbors the DNA, and a method for producing L-valine using the bacterium.

BACKGROUND ART

In the past, L-valine has been produced by a method of fermentation primarily using a microorganism belonging to the genus Brevibacterium, Corynebacterium or Serratia or a mutant thereof which produces L-valine or L-leucine (Amino acid fermentation, JAPAN SCIENTIFIC SOCIETY'S PRESS, pp.397–422, 1986). Although the conventional methods have considerably enhanced the productivity of these amino acids, the development of a more efficient, cost-effective technique is required in order to meet increasing demand for L-valine and L-leucine in the future.

As bacteria other than above-mentioned bacteria used for producion of L-valine, it is exemplified by L-valine producer belonging to the genus Escherichia which requires lipoic acid for growth and/or which is deficient in $H^+$-ATPase activity, and a bacterium belonging to the genus Escherichia which has preceding charasteristics and which is introduced an ilvGMEDA operon expressing ilvG, ilvM, ilvE and ilvD genes and not expressing threonine deaminase (WO96/06926).

The final step of L-valine biosynthesis is carried out by a group of ilvGMEDA operon-encoded enzymes. The ilvGMEDA operon includes each of ilvG, ilvM, ilvE, ilvD and ilvA genes, which encodes a large subunit and a small subunit of isozyme II of acetohydroxy-acid synthase, transaminase, dihydroxy-acid dehydratase and threonine deaminase, respectively. Of these enzymes, acetohydroxy-acid synthase, transaminase and dihydroxy-acid dehydratase catalyze the synthetic pathways from pyruvic acid to L-valine and from 2-ketobutyric acid to L-isoleucine, and threonine deaminase catalyzes the deamination from L-threonine to 2-ketobutyric acid, which is a rate-limiting step of L-isoleucine biosynthesis. Incidentally, the expression of ilvGMEDA operon suffers control (attenuation) by L-valine and/or L-isoleucine and/or L-leucine.

As acetohydroxy acid synthase concerning L-valine biosynthesis, isozyme III (hereinafter, also referred to as AHAS III) is known, apart from isozyme II (hereinafter, also referred to as AHAS II). AHAS III is coded by ilvIH operon which consists of ilvI coding for a large subunit (catalytic subunit) and ilvH coding for a small subunit (control subunit). AHAS III suffers feedback inhibition by L-valine.

Incidentally, it has been reported that the mutant ilvH gene cloned from the mutant Escherichia coli resistant to L-valine had an amino acid substitution of $^{14}$gly with asp (Vyazmensky, M. et al., Biochemistry, 35, 10339–10346 (1996)). Further, ilvH612 has been known as the AHAS III mutation (De Felice et al., J. Bacteriol., 120, 1058–1067 (1974)). The ilvH gene in the ilvIH operon of Escherichia coli MI262 (Guardiola et al., J. Bacteriol., 120, 536–538 (1974); De Felice et al., J. Bacteriol., 120, 1068–1077(1974)) contains the ilvH612 double mutation by which $^{29}$Asn is substituted with Lys and $^{92}$Gln is substituted with a termination codon(TAG), respectively.

As described above, a DNA coding for AHAS II has been utilized for breeding of L-valine producer, however, for AHAS III no case has been reported.

DISCLOSURE OF THE INVENTION

The object of the present invention, in view of the aforementioned points, is to provide a DNA coding for AHAS III which is free from a feedback inhibition by L-valine, a microorganism which harbors the DNA, and a method for producing L-valine using the bacterium.

As a result of diligent investigation in order to achieve the object described above, the present inventors found that L-valine productivity is increased when a DNA coding for valine resistant AHAS III isolated from an L-valine resistant mutant is introduced into Escherichia coli. Thus the present invention has been completed.

That is, aspects of the present invention are as follows:

(1) A DNA coding for a small subunit of acetohydroxy acid synthase isozyme III originating from Escherichia coli which has a mutation to replace an amino acid residue corresponding to serine residue at the amino acid number 17 with another amino acid residue in SEQ ID NO: 2, or both of a mutation to replace an amino acid residue corresponding to serine residue at the amino acid number 17 and a mutation to replace an amino acid residue corresponding to glycine residue at the amino acid number 14 with another amino acid residue in SEQ ID NO: 2;

(2) The DNA of (1), wherein the mutation of the amino acid residue corresponding to serine residue at the amino acid number 17 is replacement of the serine residue with phenylalanie residue and the mutation of the amino acid residue corresponding to glycine residue at the amino acid number 14 is replacement of the glycine residue with aspartic acid residue;

(3) A DNA coding for acetohydroxy acid synthase isozyme III originating from Escherichia coli which is free from an inhibition by L-valine and has an activity to catalyze two reactions to generate α-acetolactate from pyruvate and α-aceto-α-hydroxybutyrate from α-ketobutyrate and pyruvate;

(4) The DNA of (3), wherein the DNA codes for a large subunit and a small subunit of acetohydroxy acid synthase isozyme III, the small subunit having a mutation to replace an amino acid residue corresponding to serine residue at the amino acid number 17 with another amino acid residue, or a mutation to replace an amino acid residue corresponding to asparagine residue at the amino acid number 29 with another amino acid residue, or a mutation to delete a C-terminal region from the amino acid number 91 downwards, in SEQ ID NO: 2, or a combination of two or more mutations selected from the group consisting of aforementioned mutations and a mutation to replace an amino acid residue corresponding to glycine residue at the amino acid number 14 with another amino acid residue in SEQ ID NO: 2.

(5) The DNA of (4), wherein the mutation of the amino acid residue corresponding to serine residue at the amino acid number 17 is replacement of the serine residue with phenylalanine residue, the mutation of the amino acid residue corresponding to asparagine residue at the amino acid number 29 is replacement of the asparagine residue with lysine residue or tyrosine residue, and the mutation of the amino acid residue corresponding to glycine residue at the amino acid number 14 is replacement of the glycine residue with aspartic acid residue.

(6) A bacterium which harbors the DNA according to claims 1 or 3 on chromosomal DNA or plasmid in the bacterium and has an ability to produce L-valine;

(7) The bacterium of (6), wherein expression of the DNA is enhanced;

(8) The bacterium of (7), wherein the expression is enhanced by locating the DNA under the control of a potent promoter or amplifying a copy number of the DNA;

(9) A method for producing L-valine comprising the steps of cultivating the bacterium according to claim 6 in a culture medium, producing and accumulating L-valine in the culture medium, and collecting L-valine from the culture medium.

The present invention will be explained in detail below.

The first DNA of the present invention is a DNA encoding a small subunit of AHAS III which exhibits acetohydroxy synthase activity without suffering a feedback inhibition by L-valine along with a large subunit. Acetohydroxy synthase activity herein refers to an activity to catalyze two reactions to generate α-acetolactate from pyruvate, and α-aceto-α-hydroxybutyrate from α-ketobutyrate and pyruvate. AHAS III small subunit of *Escherichia coli* has an amino acid sequence depicted in SEQ ID NO: 2 in Sequence Listing.

Aforementioned mutation is selected from a mutation to replace an amino acid residue corresponding to serine residue at the amino acid number 17 with another amino acid residue in SEQ ID NO: 2, or both of a mutation to replace an amino acid residue corresponding to serine residue at the amino acid number 17 and a mutation to replace an amino acid residue corresponding to glycine residue at the amino acid number 14 with another amino acid residue in SEQ ID NO: 2. As the mutation, for the amino acid residue corresponding to serine residue at the amino acid number 17 it is preferably exemplified by replacement of the serine residue with phenylalanie residue, and for the amino acid residue corresponding to glycine residue at the amino acid number 14 it is preferably exemplified by replacement of the glycine residue with aspartic acid residue.

The second DNA of the present invention is a DNA coding for AHAS III which is free from a inhibition by L-valine and has an activity to catalyze two reactions to generate α-acetolactate from pyruvate and α-aceto-α-hydroxybutyrate from α-ketobutyrate and pyruvate. The DNA encode the large subunit and the small subunit of AHAS III, simultaneously.

The small subunit has a mutation to replace an amino acid residue corresponding to serine residue at the amino acid number 17 with another amino acid residue or a mutation to replace an amino acid residue corresponding to asparagine residue at the amino acid number 29 with another amino acid residue or a mutation to delete a C-terminal region from the amino acid number 91 downwards, in SEQ ID NO: 2, or a combination of two or more mutations selected from the group consisting of aforementioned mutations and a mutation to replace an amino acid residue corresponding to glycine residue at the amino acid number 14 with another amino acid residue in SEQ ID NO: 2. The small subunits of AHAS III which have these mutations also hereafter referred to as mutant small subunit of AHAS III. As the mutation, for the amino acid residue corresponding to serine residue at the amino acid number 17 is preferably exemplified by replacement of the serine residue with phenylalanine residue, and for the amino acid residue corresponding to asparagine residue at the amino acid number 29 it is exemplified by replacement of the asparagine residue with lysine or tyrosine residue, and for the amino acid residue corresponding to glycine residue at the amino acid number 14 it is preferably exemplified by replacement of the glycine residue with aspartic acid residue.

The DNA of the present invention was obtained from L-valine resistant mutant of *Escherichia coli*, however, it may be obtained by inducing above mutation or mutations into a DNA encoding wild type AHAS III by site-directed mutagenesis. AHAS III is coded by ilvIH operon. The ilvIH operon can be obtained by, for example, amplifying the DNA fragment which is from the promoter region to 3' end of ilvH gene by PCR using primers having sequences depicted in SEQ ID NOs: 3 and 4 from genomic DNA of *Escherichia coli* as a template. The nucleotide sequence of ilvIH operon has been known (Genbank/EMBL/DDBJ accession X55034). The nucleotide sequence of coding region of ilvH is illustrated in SEQ ID NO: 1.

The mutant small subunit of AHAS III coded by the DNA of the present invention may have an amino acid sequence which includes substitution, deletion, insertion, addition, or inversion of one or several amino acids as well as aforementioned mutation, provided that the mutant small subunit exhibits acetohydroxy acid synthase activity without suffering a feedback inhibition by L-valine along with the large subunit.

A DNA, which codes for the substantially same protein as the mutant small subunit as described above, is obtained, for example, by modifying the nucleotide sequence, for example, by means of the site-directed mutagenesis method so that one or more amino acid residues at a specified site involve substitution, deletion, insertion, addition, or inversion. DNA modified as described above may be obtained by the conventionally known mutation treatment. The mutation treatment includes a method for treating DNA coding for the small subunit in vitro, for example, with hydroxylamine, and a method for treating a bacterium belonging to the genus Escherichia harboring the DNA coding for the small subunit with ultraviolet irradiation or a mutating agent such as N-methyl-N'-nitro-N-nitrosoguanidine (NTG) and nitrous acid usually used for the mutation treatment.

The DNA, which codes for substantially the same protein as mutant small subunit of AHAS III, is obtained by expressing DNA having mutation as described above in multicopy in an appropriate cell, investigating the resistance to L-valine, and selecting the DNA which increase the resistance. Also, it is generally known that an amino acid sequence of a protein and a nucleotide sequence coding for it may be slightly different between strains, mutants or variants, and therefore the DNA, which codes for substantially the same protein, can be obtained from L-valine resistant species, strains, mutants and variants belonging to the genus Escherichia.

Specifically, the DNA, which codes for substantially the same protein as the mutant small subunit, can be obtained by isolating a DNA which hybridizes with DNA having, for example, a nucleotide sequence shown in SEQ ID NO: 1 in Sequence Listing under stringent conditions, and which codes for a protein having the acetohydroxy acid synthase activity, from a bacterium belonging to the genus Escherichia which is subjected to mutation treatment, or a spontaneous mutant or a variant of a bacterium belonging to the genus Escherichia. The term "stringent conditions" referred to herein is a condition under which so-called specific hybrid is formed, and non-specific hybrid is not formed. It is difficult to clearly express this condition by using any numerical value. However, for example, the stringent conditions include a condition under which DNAs having high homology, for example, DNAs having homology of not less than 70% with each other are hybridized, and DNAs having homology lower than the above with each other are not hybridized.

The bacterium of the present invention harbors the first DNA or the second DNA of the present invention and has an activity to produce L-valine. The bacterium is not particularly limited so long as it has a biosynthetic pathway of L-valine which acetohydroxy acid synthase concerns with. It is exemplified by a bacterium belonging to the genus Escherichia, coryneform bacteria and the genus Serratia, preferably by the genus Escherichia. A bacterium belonging to the genus Escherichia is concretely exemplified by *Escherichia coli*.

Examples of a method for introducing the DNA of the present invention into a bacterium include, for example, a method in which a bacterium is transformed with a plasmid containing the DNA of the present invention, and a method in which the DNA of the present invention is integrated into chromosomal DNA of a bacterium by homologous recombination, or the like.

It is preferable that expression of the DNA of the present invention is enhanced. The enhancement of expression is achieved by locating the DNA of the present invention under the control of a potent promoter or amplifying a copy number of the DNA. For example, lac promoter, trp promoter, trc promoter, tac promoter, $P_R$ promoter, $P_L$ promoter of lambda phage, tet promoter, amyE promoter and spac promoter are known as potent promoters. Also, it is possible to increase the copy number of the DNA of the present invention by maintaining the DNA on a multi-copy vector or introducing multiple copies of the DNA into the chromosomal DNA. The multi-copy vector is exemplified by pBR322, pTWV228, pMW119 and pUC19 or the like.

To introduce the vector containing the DNA of the present invention to a host bacterium, any known transformation methods can be employed. For instance, employable are a method of treating recipient cells with calcium chloride so as to increase the permeability of DNA, which has been reported for *Escherichia coli* K-12 [see Mandel, M. and Higa, A., *J. Mol. Biol.*, 53, 159 (1970)]; and a method of preparing competent cells from cells which are at the growth phase followed by introducing the DNA thereinto, which has been reported for *Bacillus subtilis* [see Duncan, C. H., Wilson, G. A. and Young, F. E., *Gene*, 1, 153 (1977)]. In addition to these, also employable is a method of making DNA-recipient cells into the protoplast or spheroplast which can easily take up recombinant DNAs followed by introducing the recombinant DNA into the cells, which is known to be applicable to *Bacillus subtilis*, actinomycetes and yeasts [see Chang, S. and Choen, S. N., *Molec. Gen. Genet.*, 168, 111 (1979); Bibb, M. J., Ward, J. M. and Hopwood, O. A., *Nature*, 274, 398 (1978); Hinnen, A., Hicks, J. B. and Fink, G. R., *Proc. Natl. Sci., USA*, 75, 1929 (1978)], or a method transformation used in embodiments of the present invention is the electric pulse method (refer to Japanese Patent Publication Laid-Open No. 2-207791).

Applicable method to introduce the DNA of the present invention into bacterial chromosomal DNA includes a method utilizing linearized DNA and that utilizing a plasmid containing a temperature-sensitive replication origin. Alternatively, the DNA of the present invention may be introduced into a bacterium from a bacterium harboring the DNA of the present invention on its chromosomal DNA by transduction.

In order to introduce multiple copies of the DNA of the present invention into the chromosomal DNA of a bacterium, the homologous recombination is carried out using a sequence whose multiple copies exist in the chromosomal DNA as targets. As sequences whose multiple copies exist in the chromosomal DNA, repetitive DNA, inverted repeats exist at the ends of a transposable element can be used. Also, as disclosed in Japanese Patent Publication Laid-Open No. 2-109985, it is possible to incorporate the DNA of the present invention into transposon, and allow it to be transferred to introduce multiple copies of the DNA into the chromosomal DNA.

The bacterium to which the DNA of the present invention is introduced may be a bacterium being acquired L-valine productivity by introduction of the DNA of the present invention as well as a bacterium inherently having L-valine productivity.

Examples of bacteria having L-valine productivity includes, for example, *Escherichia coli* VL1970 (U.S. Pat. No. 5,658,766). Additionally, bacteria described in W096/06926 such as L-valine producer belonging to the genus Escherichia which requires lipoic acid for growth and/or which is deficient in $H^+$-ATPase activity, or a bacterium belonging to the genus Escherichia which is introduced an ilvGMEDA operon expressing at least ilvG, ilvM, ilvE and ilvD genes are preferably used. Since the expression of ilvGMEDA operon suffers control (attenuation) by L-valine and/or L-isoleucine and/or L-leucine, it is preferable that the region which is essential for attenuation is deleted or mutated to desensitize the repression of expression by produced L-valine. Another approach suggests the introduction of the mutations (ileS or valS) affecting aminoacyl-tRNA synthases having decreased affinity (increased the Km) for the corresponding amino acids. Further, the operon which does not express active threonine deaminase is used preferably.

*Escherichia coli* VL1970 containing ileS17 mutation in which attenuation is desensitized as described above has been deposited in Russian National Collection of Industrial Microorganisms (VKPM) Depositary, GNIIgenetika, (1, Dorozhny Proezd., 1, 113545, Moscow, Russia) under the accession number of VKPM B-4411.

The methods to perform, for example, hybridization, PCR, preparation of plasmid DNA, digestion and ligation of DNA, and transformation are described by Sambrook, J., Fritsche, E. F., Maniatis, T. in *Molecular Cloning*, Cold Spring Harbor Laboratory Press, 1.21 (1989).

The production of L-valine can be performed by culturing the bacterium having L-valine productivity in a medium, to allow L-valine to be produced and accumulated in the medium, and collecting L-valine from the medium.

In the present invention, the cultivation, the collection and purification of L-valine from the medium and the like may be performed in a manner similar to the conventional fermentation method wherein an amino acid is produced using a microorganism. A medium used for culture may be either a synthetic medium or a natural medium, so long as the medium includes a carbon source and a nitrogen source and minerals and, if necessary, appropriate amounts of nutrients which the microorganism requires for growth. The carbon source may include various carbohydrates such as glucose and sucrose, and various organic acids. Depending on the mode of assimilation of the used microorganism, alcohol including ethanol and glycerol may be used. As the nitrogen source, various ammonium salts such as ammonia and ammonium sulfate, other nitrogen compounds such as amines, a natural nitrogen source such as peptone, soybean-hydrolysate and digested fermentative microorganism are used. As minerals, potassium monophosphate, magnesium sulfate, sodium chloride, ferrous sulfate, manganese sulfate, calcium carbonate, and the like are used.

The cultivation is performed preferably under aerobic conditions such as a shake culture, and an aeration and stirring culture, at a temperature of 20 to 40° C., preferably 30 to 38° C. The pH of the culture is usually between 5 and 9, preferably between 6.5 and 7.2. The pH of the culture can be adjusted with ammonia, calcium carbonate, various acids, various bases, and buffers. Usually, a 1 to 3-day cultivation leads to the accumulation of the target L-valine in the liquid medium.

After cultivation, solids such as cells can be removed from the liquid medium by centrifugation and membrane filtration, and then the target L-valine can be collected and purified by ion-exchange, concentration and crystallization methods.

BRIEF DESCRIPTION OF DRAWINGS

FIG. 1 shows PCR primer for obtaining the mutant ilvH gene containing only one mutation: $^{14}$Gly to Asp; and FIG. 2 shows PCR primer for obtaining the mutant ilvH gene containing only one mutation: $^{17}$Ser to Phe.

BEST MODE FOR CARRYING OUT THE INVENTION

The invention is described with reference to the following example:

<1> L-valine Resistant Strains of *E. coli* W3350

An L-valine resistant mutant was selected on minimal medium containing 0.1 mg/ml of L-valine from *E. coli* wild type strain W3350. Thus obtained mutant W3350 Val$_{0.1}^R$ is resistant to L-valine concentrations not higher than 1 mg/ml.

Then leucine operon (leuABCD) in which transposon Tn10 was inserted (leu::Tn10) was introduced into W3350$_{0.1}^R$ by P1 transduction. From the W3350 Val$_{0.1}^R$ leu::Tn10 transductant, a double mutant strain was induced, which grew on minimal medium containing 20 mg/ml of L-valine and 0.05 mg/ml of L-leucine.

<2> Breeding of L-valine Producing Strain VL1991

*E. coil* VL1970 (VKPM B-4411, U.S. Pat. No. 5,658,766) was introduced a gene participating resistance to high concentraion of threonine (>40 mg/ml) or homoserine (>5 mg/ml) which was isolated from a strain B3996 having a mutation (rhtA23) participating the resistance (U.S. Pat. No. 5,705,371). Thus the strain VL1971 was obtained.

Then the sucrose utilization genes from *E. coli* VL478 was introduced into VL1971 by transduction using P1 phage to obtain VL1972. And then from VL1972 a spontaneous mutant VL1991 was induced, which grew faster than the parent strain.

<3> Introduction of L-valine Resistance to VL1991

The mutations which was contained in the above-mentioned double mutant was introduced into VL1991 by P1 transduction. A spontaneous mutant which was Leu$^+$ was selected from the transductants. The mutant was designated as VL1997. Then a ilvD gene to which Tn10 had been inserted (ilvD::Tn10) was introduced into VL1997 by P1 transduction to obtain VL1997 ilvD::Tn10. VL1997 ilvD::Tn10 was then transduced with ilvGMEDA operon from *E. coli* strain B. From the thus obtained VL1998 a spontaneous mutant VL1999 was selected, which grew faster than the parent strain.

<4> L-valine Producing Strain VL1999/pVL715

The strain VL1999 was transformed with the plasmid pVL715 to obtain the recombinant valine producing strain VL1999/pVL715. The plasmid pVL715 was constructed as follows. The BamHI-XmaIII DNA fragment containing the ilv genes (ilvGMEDAYC) was cut out from the plasmid pVR12 (Gavrilova et al., *Biotechnology (in Russian)*, 4, No.5, 600–608 (1988)) which contains the genes, and subsequently inserted to pAYC32, a RSF1010 derivative (Chistoserdov and Tsygankov, Plasmid,1986, v.16, pp.161–167) substituting BamHI-XmaIII DNA fragment of pAYC32, to give the plasmid pVS712. Then the plasmid pVL715 was derived from pVS712, which suppresses the valS91 mutation affecting valyl-tRNA synthetase (U.S. Pat. No. 5,658,766) as follows. pVS712 was introduced into the valS91 mutant. The resulted strain, ValS91/pVS712, retained valine auxotrophy as the recipient strain. Then the "revertants" capable of growth in minimal medium containing no valine were selected. In some of them this property was caused by a mutation in the ilvGMEDAYC genes contained in the pVS712 plasmid. From one of the "revertant" the plasmid pVL715 was isolated. In *E. coli* strains containing pVL715 at least AHAS activity was enhanced as compared to those containing pVS712.

<5> Identification of the Mutations Conferring L-valine Resistance

From W3350 Val$_{0.1}^R$ and VL1997 ilvIH genes were cloned and sequenced. The cloning of the ilvIH genes were performed by amplifying the DNA fragments which were from the promoter region to 3' end of ilvH gene by PCR using primers having sequences depicted in SEQ ID NOs: 3 and 4. PCR was carried out by the condition: 94° C. 60 sec, 48° C. 30 sec, 72° C. 90 sec, 30 cycles. The amplified ilvIH genes were treated with Klenow fragment and cloned into HincII site of pUC19 vector to give pILVIH1 and pILVIH1, 2. In the same manner, a wild type ilvIH operon from the strain W3350 was cloned in pUC19 to obtain pILVIH.

Comparative sequence anlysis revealed that the mutant IlvIH operon of W3350 Val$_{0.1}^R$ contains substition: "C" to "T" at the nucleotide number 50 and that of VL1997 containes two substitutions: "C" to "T" at the nucleotide number 50 and "G" to "A" at the nucleotide number 41 in SEQ ID NO: 1. These mutations caused amino acid substitutions of $^{17}$Ser to Phe and $^{14}$Gly to Asp. The mutation of $^{17}$Ser to Phe and that of $^{14}$Gly to Asp may be referred to as ilvH1 mutation and ilvH2 mutation, respectively. The ilvH genes containing one or both of these mutations were designated as ilvH1, ilvH2 and ilvH1,2, respectively.

<6> Separation of ilvH1 Mutation and ilvH2 Mutation from ilvH1,2 Mutant Gene

In order to elucidate the effect of each mutation of ilvH1,2 these mutation was separated by site-directed mutagenesis using PCR.

To obtain the mutant ilvH gene containing only one mutation: $^{14}$Gly to Asp, the fact that this mutation creates a unique MluI site was utilized (FIG. 1). Thus, two primers having sequences depicted in SEQ ID NOs: 5 and 6 were synthesized.

Using above primers, a plasmid pILVIH1,2 in which ilvH1,2 gene was cloned was amplified by PCR. Thus, the linearized DNA fragment of about 5 kb which was flanked by MluI sites was produced. This PCR fragment was cut with MluI and subsequently ligated to give the circular plasmid, pILVIH2, containing only the target mutation. This was also proved by sequence analysis.

To obtain a mutant ilvH gene containing only one mutation: $^{17}$Ser to Phe, two primers having sequences depicted in SEQ ID NOs: 7 and 8 were designed (FIG. 2).

Using these primers, a plasmid pILVIH containing wild type ilvIH operon was amplified. The PCR fragment produced was flanked by StuI sites created by substitution of ATA (coding for Ile) for the adequate codon ATT. The fragment was cut with StuI and ligated to give the circular plasmid pILVIH1' containing the newly introduced mutation point $^{17}$Ser to Phe. This was substantiated by sequencing the ilvH1 gene of the plasmid.

<7> Identification of Other Mutations Conferring L-valine Resistance

From two L-valine resistant mutants derived from *E. coli* W3350 which were obtained in the same manner as described above, ilvH genes were cloned and sequenced. As a result, it was revealed that substitution of "T" for "A" at the nucleotide number 85 in SEQ ID NO: 1 was caused in one mutant and substitution of "A" for "C" at the nucleotide number 87 in SEQ ID NO: 1 was caused in another mutant. By these mutations $^{29}$Asn was replaced with Tyr or Lys, respectively. The mutation of $^{29}$Asn to Tyr and that of $^{29}$Asn to Lys may be referred to as ilvH3 and ilvH4, respectively. From these mutants the ilvIH operons were cloned in pUC19 to obtain pILVIH3 and pILVIH4, respectively.

In the same manner, ilvIH operon was cloned in pUC19 from *E. coli* MI262 (IlvI$^-$, IlvB$^-$, IlvG$^-$), obtained from *E. coli* Genetic Stock Center, which has a known mutation of AHAS III, ilvH612 (Guardiolae et al., *J. Bacteriol.*, 120, 536–538 (1974); De Felice et al., *J. Bacteriol.*, 120, 1068–1077(1974))) to obtain pILVIH262. The ilvH gene in the operon in pILVIH262 has mutations (ilvH612): "C" to "A" at the nucleotide number 87 in SEQ ID NO: 1 and "C" to "T" at the nucleotide number 274 in SEQ ID NO: 1. By these mutations $^{29}$Asn is replaced with Lys and $^{92}$Gln is substituted with a termination codon (TAG), respectively. Incidentally, the ilvI gene in the ilvIH operon of MI262 has a mutation (ilvI614) by which the expression product of the ilvI gene does not show an enzyme activity. The BamHI fragment of pILVIH262 containing mutated ilvI gene was replaced with BamHI fragment containing the wild type ilvI gene of pILVIH to obtain pILVIH612.

<8> Introduction of ilvH1 Gene to Wild Type Strain of *E. coli*

The mutant ilvH1 gene was introduced into the chromosome of *E. coli* strain W3350 using the previously described method (Parker and Marinus, 1988, Gene, v.73, pp.531–535). Thus the strain W3350 ilvH1 was obtained. It proved that this strain was resistant up to 1 mg/ml of L-valine, that is, it showed the same level of resistance as the strain W3350 Val$_{0.1}{}^R$.

Thus, by both sequence analysis of the ilvH1 gene and ilvH1 mutation which was separated from ilvH2 mutation of the ilvH1,2 mutant by site-directed mutagenesis, it was confirmed the mutation point: $^{17}$Ser to Phe, which confer upon cells low level resistance to L-valine.

<9> Effect of the Various ilvH Mutations on AHASIII Resistance to L-valine Inhibition The mutation IlvH1 ($^7$Ser to Phe), ilvH2 ($^4$Gly to Asp), ilvH3 ($^{29}$Asn to Tyr), ilvH4 ($^{29}$Asn to Lys) and ilvH612 ($^{29}$Asn to Lys and $^{92}$Gln to a termination codon, TAG), conferred enzyme AHASIII resistance to L-valine inhibition as follows. That is, *E. coli* strain MI262 deficient of AHAS activity, after the introduction of the plasmids having various ilvIH genes showed the enzyme activity with different level of resistant to L-valine (Table 1). It can also be seen that AHAS from the strains containing pILVIH2 or pILVIH612 plasmids exhibits the highest level of resistance to L-valine.

TABLE 1

Effect of the various ilvH mutations on AHAS resistance to L-valine inhibition

| Plasmid | AHAS inhibition by valine, % | |
|---|---|---|
| | 1 mM | 10 mM |
| pILVIH | 70 | >99.9 |
| pILVIH1 | 50 | 70 |
| pILVIH2 | 0 | 10 |
| pILVIH3 | 10 | 20 |
| pILVIH4 | 8 | 12 |
| pILVIH612 | 0 | 0 |

<10> Effect of the Various ilvH Mutations on L-valine Production

The effect of various ilvH mutations on L-valine production was examined. The mutations were introduced into the chromosome of the strains VL1970 and VL1999/pVL715. Incidentally, the parent strain (W3350) of the strains VL1970 and VL1999 does not express an active acetohydroxy acid syntase II (AHAS II), since the parent strain has a frame-shift mutation in the ilvG gene. One the other hand the strains VL1970 and VL1999 express an active AHAS II.

After the introduction of various ilvH mutations into the strain VL1970 the new strains VL1970 ilvH1, VL1970 ilvH1,2, VL1970 ilvH3, VL1970 ilvH4, VL1970 ilvH612 were obtained. Besides, after the introduction of various ilvH mutations into the strain VL1999/pVL715 the new strains VL1999 ilvH1,2/pVL715, VL1999 ilvH3/pVL715, VL1999 ilvH612/pVL715 were obtained. These strains and the respective parental strains were each cultivated at 37° C. for 18 hours in a nutrient broth, and 3 ml of a fermentation medium having the following composition in a 20×200 mm test tube, was inoculated with 0.3 ml of the obtained culture, and cultivated at 37° C. for 72 hours with a rotary shaker (250 r.p.m.). After the cultivation, an accumulated amount of valine in the medium and an absorbance at 560 nm of the medium were determined by known methods.

The results are presented in Table 2 and Table 3. In these tables, ilvH$^+$ indicates the wild type ilvH gene.

Fermentation medium composition (g/L):

| | |
|---|---|
| Glucose | 80 |
| (NH$_4$)$_2$SO$_4$ | 22 |
| K$_2$HPO$_4$ | 2 |
| NaCl | 0.8 |
| MgSO$_4$*7H$_2$O | 0.8 |
| FeSO$_4$*7H$_2$O | 0.02 |
| MnSO$_4$*5H$_2$O | 0.02 |
| Thiamine hydrochloride | 0.2 |
| Yeast Extract (Sigma) | 1.0 |
| CaCO$_3$ | 30 |
| (CaCO$_3$ was separately sterilized) | |

TABLE 2

Effect of the different ilvH mutations on L-valine production by the strains VL1970

| Strain | OD$_{560}$ | L-Valine (g/L) |
|---|---|---|
| VL1970 | 19.4 | 10.2 |
| VL1970ilvH1 | 20.1 | 11.4 |
| VL1970ilvH1,2 | 19.5 | 12.6 |
| VL1970ilvH3 | 18.2 | 12.62 |
| VL1970ilvH4 | 17.2 | 11.7 |
| VL1970ilvH612 | 18.4 | 12.8 |

TABLE 3

L-valine production by the strain VL1999/pVL7215 containing different mutations in ilvH gene

| Strain | OD$_{560}$ | L-Valine(g/L) |
|---|---|---|
| VL1999 ilvH+/pVL715 | 17.6 | 18.7 |
| VL1999 ilvH1,2/pVL715 | 18.9 | 23.4 |
| VL1999 ilvH3/pVL715 | 19.4 | 20.6 |
| VL1999 ilvH6l2/pVL715 | 17.7 | 20.2 |

It can be seen from the Table 2 and Table 3 that the introduction of the ilvH mutations described above improved valine productivity of the respective valine producing strains. Also, the combination of ilvH1 and ilvH2 mutations may give the best result.

The pUC19 derivatives which have ilvIH operons containing various mutant ilvH genes were introduced into the strain W3350. Incidentally, the strain W3350 does not express an active AHAS II, since the strain has a frame-shift mutation in the ilvG gene. It can be seen from the Table 4 that the obtained transformants produced L-valine, and that the strain containing the plasmid pILVIH1,2 was the most productive.

TABLE 4

L-valine production by the strain W3350 harboring plasmids with different mutant ilvH genes

| Strain | OD$_{560}$ | L-Valine (g/L) |
|---|---|---|
| W3350 | 21.4 | 0 |
| W3350/pILVIH1 | 13.8 | 2.3 |
| W3350/pILVIH1,2 | 10.5 | 8.2 |
| W3350/pILVIH3 | 11.7 | 5.9 |
| W3350/pILVIH4 | 16.4 | 5.5 |

Previously the present inventors observed that in the course of L-valine fermentation the activity of AHAS in the producer's cells (mainly presented by AHAS II) was gradually decreasing. It was shown that half-life of AHAS III at 45° C. was 144 min., and that of AHAS II was 44 min. (Alexander-Caudle et al., *J. Bacteriol.* 172, 3060–3065 (1990)). It may be suggested that this increased thermostability of AHAS III reflects the general increased stability of the enzyme. Therefore it is thought that L-valine-resistant AHAS III has positive effect on L-valine production because of its increased stability as compared to AHAS II.

---

What is claimed is:

1. An isolated DNA molecule encoding a small subunit of acetohydroxy acid synthase isozyme III originating from *Escherichia coli*, which has a mutation selected from the group consisting of:
   a) a mutation that replaces the serine at amine acid number 17 in SEQ ID NO: 2 with an amino acid other than serine and
   b) a mutation that replaces both (i) the serine residue at amino acid number 17 in SEQ ID NO: 2 with an amino acid other than serine and (ii) the glycine residue at the amino acid number 14 in SEQ ID NO: 2 with an amino acid other than glycine,
   wherein the unmutated sequence of acetohydroxy acid synthase isozyme III is SEQ ID NO:2.

2. The isolated DNA according to claim 1, wherein the mutation at amino acid number 17 replaces serine with a phenylalanine residue and the mutation at the amino acid number 14 replaces glycine with an aspartic acid residue.

3. The isolated DNA according to claim 1, wherein the mutation at amino acid number 14 replaces glycine with an aspartic acid residue.

4. Tue isolated DNA according to claim 1, wherein the mutation at amino acid number 17 replaces serine with a phenylalanine residue.

5. An isolated bacterium which harbors the DNA according to claim 1 on chromosomal DNA or plasmid in said bacterium and has an ability to produce L-valine.

6. The bacterium according to claim 5, wherein expression of said DNA is enhanced by locating said DNA under the control of a potent promoter or amplifying the copy number of said DNA.

7. A method for producing L-valine comprising the steps of cultivating the bacterium according to claim 5 in a culture medium producing and accumulating L-valine in the culture medium, and collecting L-valine from the culture medium.

8. An isolated DNA encoding a large subunit and a mutated small subunit of acetohydroxy acid synthase isozyme III originating from *Escherichia coli*,
   wherein the unmutated sequence of the small subunit of acetohydroxy acid synthase isozyme III is SEQ ID NO:2 and wherein said small subunit has a mutation that replaces the glycine residue at amino acid number 14 in SEQ ID NO: 2 with an amino acid other than glycine and has at least one mutation selected from the group consisting of:
   a) a mutation that replaces the serine residue at amino acid number 17 in SEQ ID NO: 2 with an amino acid other than serine,
   b) a mutation that replaces the asparagine residue at amino acid number 29 in SEQ w NO: 2 with an amino acid other than asparagine, and
   c) a mutation that replaces the glutamine residue at amino acid number 92 in SEQ ED NO: 2 with a stop codon, wherein the large subunit and the mutated small subunit together constitute acetohydroxy acid synthase isozyme III that catalyzes the generation of (i) α-acetolactate from pyruvate and (ii) α-aceto-α-hydroxybutyrate from α-ketobutyrate and pyruvate;

and wherein L-valine feedback inhibition of acetohydroxy acid synthase activity is reduced by said mutation as compared to the unmutated acetohydroxy acid synthase.

9. The isolate DNA according to claim 8, wherein the mutation at amino number 17 replaces serine with a phenylalanine residue, the mutation at amino acid number 29 replaces asparagine with a lysine residue or a tyrosine residue, and the mutation at amino acid number 14 replaces glycine with an aspartic acid residue.

10. The isolated DNA according to claim 8, wherein the mutation at amino acid number 14 replaces glycine with an aspartic acid residue.

11. The isolated DNA according to claim 8, wherein the mutation at amino acid number 17 replaces serine with a phenylalanine residue.

12. The isolated DNA according to claim 8, wherein the mutation at amino acid number 29 replaces asparagine with a tyrosine residue.

13. The isolated DNA according to claim 8, wherein the mutation at amino acid number 29 replaces asparagine with a lysine residue.

14. An isolated, bacterium which harbors the DNA according to claim 8 on chromosomal DNA or plasmid in said bacterium and has an ability to produce L-valine.

15. The bacterium according to claim 14, wherein expression of said DNA is enhanced by locating said DNA under the control of a potent promoter or amplifying a copy number of said DNA.

16. A method for producing L-valine comprising the steps of cultivating the bacterium according to claim 14 in a culture medium, producing and accumulating L-valine in the culture medium, and collecting L-valine from the culture medium.

* * * * *